(12) United States Patent
Tal et al.

(10) Patent No.: US 12,102,776 B2
(45) Date of Patent: Oct. 1, 2024

(54) EMBOLIZATION MICROCATHETER HEAD HAVING SLITTED PATTERN

(71) Applicant: ACCURATE MEDICAL THERAPEUTICS LTD., Rehovot (IL)

(72) Inventors: Michael Gabriel Tal, Savyon (IL); Eran Miller, Moshav Beit Elazari (IL)

(73) Assignee: ACCURATE MEDICAL THERAPEUTICS LTD., Rehovot (IL)

(*) Notice: Subject to any disclaimer, the term of this patent is extended or adjusted under 35 U.S.C. 154(b) by 30 days.

(21) Appl. No.: 17/464,993

(22) Filed: Sep. 2, 2021

(65) Prior Publication Data
US 2021/0393917 A1 Dec. 23, 2021

Related U.S. Application Data

(63) Continuation of application No. 16/099,166, filed as application No. PCT/IL2017/050489 on May 3, 2017, now Pat. No. 11,129,960.
(Continued)

(51) Int. Cl.
*A61M 25/00* (2006.01)
*A61B 17/12* (2006.01)

(52) U.S. Cl.
CPC ..... *A61M 25/007* (2013.01); *A61B 17/12022* (2013.01); *A61B 17/12186* (2013.01);
(Continued)

(58) Field of Classification Search
CPC ........... A61M 25/007; A61M 25/0045; A61M 25/005; A61M 25/0051; A61M 25/0074;
(Continued)

(56) References Cited

U.S. PATENT DOCUMENTS

| 3,888,249 A | 6/1975 | Spencer |
| 5,178,611 A | 1/1993 | Rosenberg |

(Continued)

FOREIGN PATENT DOCUMENTS

| CA | 2382871 A1 | 3/2001 |
| CN | 102665608 A | 9/2012 |

(Continued)

OTHER PUBLICATIONS

Applicant Initiated Interview Summary (PTOL-413) dated Jun. 8, 2020 for U.S. Appl. No. 15/554,825.
(Continued)

*Primary Examiner* — Robert J Utama
*Assistant Examiner* — Hamza A Darb
(74) *Attorney, Agent, or Firm* — Kaplan Breyer Schwarz, LLP (57) ABSTRACT

An embolization microcatheter having an elongated microcatheter body configured for passing therein a suspension of particles suspended in a suspension fluid; and a microcatheter head connected to a distal end of said microcatheter body and comprising a proximal head section and a distal head section, wherein the proximal head section includes a proximal wall forming a proximal section lumen, the proximal wall having a plurality of through-holes, wherein the distal head section includes a distal wall forming a distal section lumen, and a suspension delivery opening at a distal end of the distal end section; wherein the distal section is devoid of through-holes, and wherein each of the plurality of through-holes are shaped and/or sized to allow passage therethrough of the suspension fluid while blocking passage of the particles suspended therein.

13 Claims, 5 Drawing Sheets

Related U.S. Application Data (60) Provisional application No. 62/331,724, filed on May 4, 2016.

(52) U.S. Cl.
CPC ...... *A61M 25/0045* (2013.01); *A61M 25/005* (2013.01); *A61M 25/0051* (2013.01); *A61M 25/0074* (2013.01); *A61M 25/008* (2013.01); *A61B 2017/1205* (2013.01); *A61M 25/0013* (2013.01); *A61M 2025/0042* (2013.01); *A61M 2025/0059* (2013.01)

(58) Field of Classification Search
CPC ............ A61M 25/008; A61M 25/0013; A61M 2025/0042; A61M 2025/0059; A61M 2025/006; A61B 17/12022; A61B 17/12186; A61B 2017/1205; A61B 17/12109
See application file for complete search history.

(56) References Cited

U.S. PATENT DOCUMENTS

| | | | |
|---|---|---|---|
| 5,318,032 | A | 6/1994 | Lonsbury et al. |
| 5,514,092 | A | 5/1996 | Forman et al. |
| 5,573,520 | A | 11/1996 | Schwartz et al. |
| 5,601,539 | A | 2/1997 | Corso, Jr. |
| 5,749,894 | A | 5/1998 | Engelson |
| 5,817,057 | A | 10/1998 | Berenstein et al. |
| 5,833,671 | A | 11/1998 | Macoviak et al. |
| 5,964,223 | A | 10/1999 | Baran |
| 6,146,373 | A | 11/2000 | Cragg et al. |
| 6,280,434 | B1 | 8/2001 | Kinoshita et al. |
| 6,695,809 | B1 | 2/2004 | Lee |
| 8,500,775 | B2 | 8/2013 | Chomas et al. |
| 8,846,099 | B2 | 9/2014 | Nadal Ginard |
| 9,345,857 | B2 | 5/2016 | Latere Dwan'Isa et al. |
| 9,468,739 | B2 | 10/2016 | Sutherland et al. |
| 10,398,875 | B2 | 9/2019 | Tal et al. |
| 11,129,960 | B2 * | 9/2021 | Tal ..................... A61M 25/0051 |
| 2001/0036451 | A1 | 11/2001 | Goupil et al. |
| 2002/0143348 | A1 | 10/2002 | Wallace et al. |
| 2002/0197246 | A1 | 12/2002 | Toombs |
| 2003/0045842 | A1 | 3/2003 | Kawakita et al. |
| 2003/0130682 | A1 | 7/2003 | Broome et al. |
| 2004/0006306 | A1 | 1/2004 | Evans et al. |
| 2004/0122362 | A1 | 6/2004 | Houser et al. |
| 2004/0176743 | A1 | 9/2004 | Morris et al. |
| 2005/0177131 | A1 * | 8/2005 | Lentz ............... A61M 25/0054 604/525 |
| 2006/0004316 | A1 | 1/2006 | Difiore et al. |
| 2007/0073271 | A1 | 3/2007 | Brucker et al. |
| 2007/0135791 | A1 | 6/2007 | Slater et al. |
| 2007/0225634 | A1 | 9/2007 | Ferren et al. |
| 2007/0225637 | A1 | 9/2007 | Ono et al. |
| 2008/0039786 | A1 | 2/2008 | Epstein et al. |
| 2008/0172011 | A1 | 7/2008 | Heroux et al. |
| 2008/0188831 | A1 | 8/2008 | Bonnette et al. |
| 2008/0188928 | A1 | 8/2008 | Salahieh et al. |
| 2011/0082427 | A1 | 4/2011 | Golzarian et al. |
| 2011/0137399 | A1 | 6/2011 | Chomas et al. |
| 2011/0152741 | A1 | 6/2011 | Banchieri et al. |
| 2011/0182998 | A1 | 7/2011 | Reb et al. |
| 2011/0245766 | A1 | 10/2011 | Leonard et al. |
| 2011/0251629 | A1 | 10/2011 | Galdonik et al. |
| 2012/0041419 | A1 | 2/2012 | Blanchard et al. |
| 2012/0116351 | A1 | 5/2012 | Chomas et al. |
| 2012/0245562 | A1 | 9/2012 | Bihlmaier |
| 2013/0144267 | A1 * | 6/2013 | Chan ................. A61M 25/0054 156/196 |
| 2013/0267845 | A1 | 10/2013 | Howle et al. |
| 2013/0338643 | A1 | 12/2013 | De Silva |
| 2015/0051583 | A1 | 2/2015 | Horvath et al. |
| 2015/0088090 | A1 | 3/2015 | Macy, Jr. |
| 2016/0074621 | A1 | 3/2016 | Yao et al. |
| 2017/0368306 | A1 * | 12/2017 | Tal ..................... A61M 25/0067 |
| 2018/0049747 | A1 | 2/2018 | Tal et al. |

FOREIGN PATENT DOCUMENTS

| | | |
|---|---|---|
| EP | 1857134 A1 | 11/2007 |
| EP | 2010263 A2 | 1/2009 |
| EP | 2777738 A2 | 9/2014 |
| JP | 09-508557 A | 9/1997 |
| JP | 11-276592 | 10/1999 |
| JP | 11-513293 A | 11/1999 |
| JP | 2007-511290 A | 5/2007 |
| JP | 2008-086765 A | 4/2008 |
| JP | 2008-509781 A | 4/2008 |
| JP | 2011-178784 A | 9/2011 |
| JP | 2011-529946 A | 12/2011 |
| JP | 2013-512735 A | 4/2013 |
| WO | 96/04952 A1 | 2/1996 |
| WO | 97/21455 A1 | 6/1997 |
| WO | 98/33544 A1 | 8/1998 |
| WO | 01/32240 A1 | 5/2001 |
| WO | 2004/071495 A1 | 8/2004 |
| WO | 2005/005198 A2 | 1/2005 |
| WO | 2005/049110 A2 | 6/2005 |
| WO | 2005/058198 A1 | 6/2005 |
| WO | 2007/067255 A1 | 6/2007 |
| WO | 2007/121143 A2 | 10/2007 |
| WO | 2008/067362 A2 | 6/2008 |
| WO | 2009/132065 A1 | 10/2009 |
| WO | 2010/026578 A1 | 3/2010 |
| WO | 2010/125159 A1 | 11/2010 |
| WO | 2011/068924 A1 | 6/2011 |
| WO | 2011/091275 A1 | 7/2011 |
| WO | 2013/126456 | 8/2013 |
| WO | 2013/184782 A2 | 12/2013 |
| WO | 2014/047179 A1 | 3/2014 |
| WO | 2015/001456 A1 | 1/2015 |
| WO | 2015/195625 A1 | 12/2015 |
| WO | 2015/195646 A1 | 12/2015 |
| WO | 2016/110824 A1 | 7/2016 |
| WO | 2016/139597 A2 | 9/2016 |
| WO | 2016/139606 A1 | 9/2016 |
| WO | 2017/191636 A1 | 11/2017 |
| WO | 2019/087191 A1 | 5/2019 |

OTHER PUBLICATIONS

Authorized Officer: Aharony Meytal, "International Search Report and Written Opinion" issued in co-pending PCT application No. PCT/IL2017/050489, dated Aug. 20, 2017, 8 pages.
Final Office Action issued in U.S. Appl. No. 15/554,825 dated Oct. 7, 2020.
Non-Final Rejection dated Jul. 25, 2018 in U.S. Appl. No. 15/542,427.
Examiner Interview Summary dated Dec. 28, 2020 for U.S. Appl. No. 16/099,166.
Extended European Search Report issued in counterpart EP Patent Application No. 18874080.7 dated Nov. 30, 2020.
Final Rejection dated Oct. 7, 2020 for U.S. Appl. No. 15/554,825.
International Search Report of PCT/IB2016/051175 Completed: Sep. 5, 2016; dated Sep. 15, 2016 9 pages.
International Search Report of PCT/IB2016/050087 Completed Mar. 15, 2016; dated Mar. 22, 2016, 4 pages.
International Search Report of PCT/IB2016/051175 Completed: Sep. 5, 2016; dated Sep. 15, 2016 9 pages.
Non-Final Rejection dated Mar. 10, 2020 for U.S. Appl. No. 15/554,825.
Non-Final Rejection dated Oct. 22, 2020 for U.S. Appl. No. 16/099,166.
Notice of Allowance dated May 19, 2021 for U.S. Appl. No. 16/099,166.
Requirement for Restriction/Election dated Dec. 30, 2019 for U.S. Appl. No. 15/554,825.
Written Opinion of International Searching Authority of PCT/IB2016/050087 Completed Mar. 15, 2016; dated Mar. 22, 2016, 6 pages.

(56) References Cited

OTHER PUBLICATIONS

Written Opinion of the International Searching Authority of PCT/IB2016/051175 Completed: Sep. 5, 2016; dated Sep. 15, 2016 13 pages.
(Guerbet, Roissy, France), SEQURE Reflux Control Microcatheter. 'Deliver more. Reduce the risk of nontarget embolization', Sep. 30, 2020.
Advisory Action (PTOL-303) Mailed on Jan. 15, 2021 for U.S. Appl. No. 15/554,825, 3 page(s).
Examiner Interview Summary Record (PTOL-413) Mailed on Jan. 15, 2021 for U.S. Appl. No. 15/554,825, 1 page(s).
Examiner Interview Summary Record (PTOL-413) Mailed on Jan. 25, 2022 for U.S. Appl. No. 15/554,825, 1 page(s).
Examiner Interview Summary Record (PTOL-413) Mailed on Jun. 11, 2021 for U.S. Appl. No. 15/554,825, 3 page(s).
Final Rejection Mailed on Sep. 24, 2021 for U.S. Appl. No. 15/554,825, 15 page(s).
Non-Final Rejection Mailed on Apr. 22, 2021 for U.S. Appl. No. 15/554,825, 21 page(s).
Notice of Allowance and Fees Due (PTOL-85) Mailed on Apr. 27, 2022 for U.S. Appl. No. 15/554,825, 2 page(s).
Notice of Allowance and Fees Due (PTOL-85) Mailed on Jan. 25, 2022 for U.S. Appl. No. 15/554,825, 15 page(s).
Office Action Appendix Mailed on Jan. 25, 2022 for U.S. Appl. No. 15/554,825, 4 page(s).
Office Action Appendix Mailed on Jun. 8, 2020 for U.S. Appl. No. 15/554,825, 4 page(s).
Office Action Appendix Mailed on Jun. 11, 2021 for U.S. Appl. No. 15/554,825, 4 page(s).

* cited by examiner

SECTION C-C
FIG. 5B

EMBOLIZATION MICROCATHETER HEAD HAVING SLITTED PATTERN

CROSS-REFERENCE TO RELATED APPLICATIONS

The present application is a continuation of U.S. patent application Ser. No. 16/099,166, now U.S. Pat. No. 11,129,960 B2 issued on Sep. 28, 2021, which is a 371 of international application PCT/IL2017/050489, which claims the priority benefit of U.S. provisional application 62/331,724, the entire disclosures of which are incorporated herein by reference.

FIELD OF THE INVENTION

The present invention, in some embodiments thereof, relates to infusion catheters, and more particularly, but not exclusively, to embolization microcatheters with side openings.

BACKGROUND OF THE INVENTION

Therapeutic embolization is a nonsurgical, minimally invasive procedure in which one or more agents are dispersed in a target blood vessel for selective vascular occlusion and for preventing blood supply to a specific area or organ. The procedure is used for treatment of several medical conditions, for instance, blocking an aneurysm and shrinking tumors in the liver, kidney and other organs.

Several types of agents may be used during embolization, including coils, gelfoam, polyvinyl alcohol, alcohol, tissue adhesives and different types of microspheres. The microspheres may be embolic and/or drug eluting, as in the case of chemo-embolization, which uses embolic particles coated with chemotherapeutic agents, and radio embolization, which uses radioactive microspheres.

Reflux, back flow in a vessel, often occurs during embolization procedures. Reflux may cause non-target delivery of embolic agents into healthy surrounding tissue thus resulting in potential side effects and varying complications.

It is within the scope of the present invention to provide concepts and designs for embolization microcatheters with inherent capabilities in diminishing risk of non-targeted embolization.

SUMMARY OF THE INVENTION

The present invention, in some embodiments thereof, relates to infusion catheters, and more particularly, but not exclusively, to embolization microcatheters with side openings.

According to an aspect of some embodiments of the present invention, there is provided an embolization microcatheter, that includes:
  an elongated microcatheter body connectable at a proximal body end thereof to a suspension reservoir and configured for passing therein a premade suspension of particles suspended in a suspension fluid; and
  a microcatheter head connected to a distal body end of said microcatheter body, the microcatheter head comprising a proximal head section and a distal head section, said distal end head section terminating with a head tip. The proximal head section includes a proximal section lumen opened laterally with a plurality of through-holes allowing outflow of the suspension fluid. The distal head section includes a distal section lumen sealed laterally and having a frontal opening at its end allowing outflow of the suspension including particles.

In some embodiments, each said side through-hole is shaped and/or sized to allow passage therethrough of the suspension fluid while blocking passage of the embolization particles.

In some embodiments, each of said through-holes has a smallest cross sectional dimension in a range of between about 10 microns and about 700 microns.

In some embodiments, at least one of said through-holes has a smallest cross sectional dimension equal to or less than about 50 microns. In some embodiments, each of said through-holes has a smallest cross sectional dimension equal to or less than about 50 microns.

In some embodiments, each of said through-holes has a smallest cross sectional dimension in a range of between about 15 microns and about 40 microns, or in a range of between about 40 microns and about 100 microns, or in a range of between about 100 microns and about 700 microns.

In some embodiments, at least one of said through-holes has a smallest cross sectional dimension equal to or more than about 25 microns. In some embodiments, each of said through-holes has a smallest cross sectional dimension equal to or less than about 25 microns.

In some embodiments, a minimal diameter of said proximal section lumen is substantially greater than a maximal diameter of said distal section lumen. Optionally, at least part of the distal section lumen may have a constricted diameter equal to or smaller than said maximal diameter. According to some embodiments, the distal section, or at least the constricted part thereof, may have a length of about 15 mm, about 10 mm, about 7 mm or about 5 mm. Each possibility is a separate embodiment. Optionally, said constricted diameter is from about 1 mm to about 20 mm, optionally particularly about 10 mm or less or about 7 mm or less. Optionally, said constricted length extends between said proximal head section and said suspension delivery opening at the distal end of the microcatheter head.

According to some embodiments, the length of the distal end section, as well as the number and/or size of the plurality of through-holes, may differ according to the size and characteristics of the embolization particles for which it is used.

As a non-limiting example, microcatheters for delivering 70-700 micron embolization particles (e.g. 250 micron embolization particles) may include 5-100, 10-50, 15-30, 20-30 or any other suitable amount of slits in the range of 5-100 slits (e.g. 27 slits). According to some embodiments, the slits may have a width in the range of 25-75 microns (e.g. about 50 microns) and a length in the range of 400-800 microns (e.g. about 600 microns). Additionally or alternatively, the microcatheters for delivering 70-700 micron embolization particles may have a distal end section lumen diameter essentially equal to (or similar to) the diameter of the proximal end section lumen (i.e. non-restricted). Additionally or alternatively, the microcatheters for delivering 70-700 micron embolization particles may have a distal end section length of 5-10 mm (e.g. about 7 mm). It is understood that such proportions may ensure that the flow of suspension fluid through the through-holes is sufficient to generate a fluid flow barrier preventing back flow of particles delivered through the suspension delivery opening, while retaining a sufficient flow for optimal delivery of embolization particles through the suspension delivery opening.

As another non-limiting example, microcatheters for delivering 20-200 micron embolization particles (e.g. 40 micron embolization particles) may include 5-100, 10-75, 20-60, 25-50 or any other suitable amount of slits in the range of 5-100 slits (e.g. 50 slits). According to some embodiments, the slits may have a width in the range of 10-30 microns (e.g. about 18 microns) and a length in the range of 200-800 micron (e.g. about 800 microns). Additionally or alternatively, the microcatheters for delivering 20-200 micron embolization particles may have a distal end section lumen diameter which (at least along part of its length) is smaller than the diameter of the proximal end section lumen (also referred to herein as a "restricted lumen" or a "restrictor section"). Additionally or alternatively, the length of the distal end section of microcatheters for delivering 20-200 micron embolization particles may be in the range of 4 mm-10 mm or optionally more than 7 mm (e.g. about 10 mm). As above, such proportions may ensure that the flow of suspension fluid through the through-holes is sufficient to generate a fluid flow barrier preventing back flow of particles delivered through the suspension delivery opening, while retaining a sufficient flow for optimal delivery of embolization particles through the suspension delivery opening.

As another non-limiting example, microcatheters for delivering 500-900 micron embolization particles (e.g. 700 micron embolization particles) may include 5-50, 10-40 or any other number of slits in the range of 5-50 slits having a width in the range of 50-100 microns and a length in the range of 200-800 micron (e.g. about 600 microns). Additionally or alternatively, the microcatheters for delivering 500-900 micron embolization particles may have a distal end section lumen diameter essentially equal to (or similar to) the diameter of the proximal end section lumen (i.e. non-restricted). Additionally or alternatively, the microcatheters for delivering 500-900 micron embolization particles may have a distal end section length in the range of 4 mm-10 mm or optionally a length of less than 7 mm. As above, such proportions may ensure that the flow of suspension fluid through the through-holes is sufficient to generate a fluid flow barrier preventing back flow of particles delivered through the suspension delivery opening, while retaining a sufficient flow for optimal delivery of embolization particles through the suspension delivery opening.

In some embodiments, said proximal section is about 2.5 mm to about 15 mm in length. In some embodiments, the length of said microcatheter head is between about 5 and about 30 mm, or optionally between about 10 and about 15 mm.

In some embodiments, the maximal outer diameter of said microcatheter head is about 10 mm or less, about 5 mm or less, about 2 mm or less, about 1.5 mm or less, or about 1 mm or less. Each possibility is a separate embodiment.

In some embodiments, each said side through-hole may be a slit with a gap having a width less than a minimal diameter of said particles, so as to block passage thereof.

In some embodiments, said side through-holes are distributed along and around a length of said proximal head section in a form of a slitted pattern, said slitted pattern including a plurality of longitudinally spaced circumferential segments, each circumferential segment including a number of circumferentially spaced slits, i.e. radial slits.

According to some embodiments, the slits may be radial (i.e. perpendicular to the longitudinal axis of the catheter. In some embodiments, the length of each said slit is between about 0.2 mm to about 1 mm or about 0.4 mm to 0.8 mm.

In some embodiments, each two adjacent slits in a circumferential segment are spaced by about 50 microns to about 250 microns.

In some embodiments, two adjacent circumferential segments are spaced by about 50 microns to about 250 microns.

In some embodiments, each two adjacent slits, between two adjacent circumferential segments may be radially offset one with respect to the other.

In some embodiments, said slitted pattern allows bending or curving of the microcatheter head between adjacent circumferential segments. In some embodiments, the bending or curving allows a maximal bend radius before kinking of at least about 0.5 mm, between said head tip relative to said distal body end (i.e. the distal end of the catheter to which it is attached). According to some embodiments, the spacing between adjacent circumferential segments is configured to prevent kinking.

In some embodiments, a total opened area of all said through-holes is between about 0.1 mm$^2$ and about 7.5 mm$^2$. In some embodiments, a total opened area of all said through-holes is between about 2.5 mm$^2$ and about 7.5 mm$^2$. In some embodiments, a total opened area of all said through-holes is between about 0.5 mm$^2$ and about 1.5 mm$^2$.

In some embodiments, a total open area of said suspension delivery opening (also referred to herein as the end opening) is between about 0.1 mm$^2$ and about 1 mm$^2$.

In some embodiments, the total open area, dimensions and/or shapes of said through-holes, or/and dimensions (including length and internal diameter) and/or shape of said proximal section lumen, and/or dimensions (including length and internal diameter) and/or shape of said distal section lumen, and/or total opened area, dimensions and/or shape of said suspension delivery opening, is so chosen as to maintain a fixed ratio of suspension fluid flow rate, through said through-holes, relative to suspension fluid flow rate, through said suspension delivery opening.

In some embodiments, said fixed ratio is about 1:1, or optionally at least about 2:1. According to some embodiments, the ration is in the range of 1:4-4:1. According to some embodiments, the ration is in the range of 1:3-3:1.

In some embodiments, said microcatheter head is formed as a single part.

In some embodiments, said proximal head section and said distal head section may be formed as separate elements, assembled (e.g. molded or otherwise attached together) when forming said microcatheter head.

In some embodiments, said proximal head section includes at least one layer of polymeric tubing with a wall perforated by said through-holes. Optionally, said polymeric tubing includes an inner polymeric liner, optionally made from PTFE, and an outer polymeric extrusion, optionally made from thermoplastic elastomer such as thermoplastic polyurethane or polyether block amide. According to some embodiments, the through holes extend through both said outer polymeric extrusion and said inner polymeric liner. Optionally, said polymeric tubing is reinforced with a coil, in which case the through-holes may be formed in-between windings of said coil, and/or overlapping with windings of said coil, while leaving the coil intact.

In some embodiments, said proximal head section and/or said distal head section may include or be made from a metal tubing, optionally formed of stainless steel, Cobalt Chrome or Ni—Ti alloy.

In some embodiments, said proximal head section and/or said distal head section includes a hydrophilic coating, perforated by said through-holes.

In some embodiments, said proximal head section includes embedded tungsten powder, platinum iridium (or any other material suitable as a radio-opaque marker).

According to some embodiments the marker material may be perforated or non-perforated by said through-holes.

In some embodiments, said distal head section includes embedded tungsten powder, platinum iridium (or any other material suitable as a radio-opaque marker).

In some embodiments, said proximal head section has a substantially elastic wall and said distal head section has a substantially more rigid wall. Such configuration may enable the inner diameter of the proximal head section to expand while the inner diameter of the distal head section substantially maintains its size, when suspension fluid passes therethrough. In some embodiments, the expanded inner diameter obtained during infusion, is substantially larger than the maximal inner diameter of the distal head section, such that the flow rate of the suspension fluid through the through holes increases gradually along with the expansion of the inner diameter of the proximal head section until reaching a predetermined flow rate ratio between the through holes and the suspension delivery opening. According to some embodiments, the proximal head section may be expandable. Optionally, the predetermined flow rate ratio is in the range of 4:1-1:4, 3:1-1:3 or 1:2-2:1. According to some embodiments, the predetermined flow rate ration is 1:1.

Unless otherwise specifically defined or stated herein, technical or/and scientific words, terms, or/and phrases, used herein have the same or similar meaning as commonly understood by one of ordinary skill in the art to which the invention pertains. Exemplary embodiments of methods (steps, procedures), apparatuses (devices, systems, components thereof), equipment, and materials, illustratively described herein are exemplary and illustrative only and are not intended to be limiting. Although methods, apparatuses, equipment, and materials, equivalent or similar to those described herein can be used in practicing or/and testing embodiments of the invention, exemplary methods, apparatuses, equipment, and materials, are illustratively described below.

Implementation of some embodiments of the invention can involve performing or completing selected tasks manually, automatically, or a combination thereof. Moreover, according to actual instrumentation and equipment of some embodiments of the invention, several selected tasks could be implemented by hardware, by software, by firmware, or a combination thereof, using an operating system.

BRIEF DESCRIPTION OF THE DRAWINGS

Some embodiments of the present invention are herein described, by way of example only, with reference to the accompanying drawings. With specific reference now to the drawings in detail, it is stressed that the particulars shown are by way of example and for purposes of illustrative description of some embodiments of the present invention. In this regard, the description taken together with the accompanying drawings make apparent to those skilled in the art how some embodiments of the present invention may be practiced.

In the drawings.

DETAILED DESCRIPTION OF THE INVENTION

The present invention, in some embodiments thereof, relates to infusion catheters, and more particularly, but not exclusively, to embolization microcatheters with side openings.

For purposes of further understanding exemplary embodiments of the present invention, in the following illustrative description thereof, reference is made to the figures (FIGS. 1 through 5). Throughout the following description and accompanying drawings, same reference numbers refer to same components, elements, or features. It is to be understood that the invention is not necessarily limited in its application to particular details of construction or/and arrangement of exemplary device, apparatus, or/and system components, set forth in the following illustrative description. The invention is capable of other exemplary embodiments or of being practiced or carried out in various ways.

In an aspect of some embodiments there is provided an embolization microcatheter configured for delivering particles (e.g., embolization beads) suspended in a suspension fluid. The embolization microcatheter head is provided with a suspension delivery opening located at a tip of the microcatheter head, as well as side through-holes (also referred to herein as "slits") covering a portion of the microcatheter head, the through-holes sized and configured for delivering therethrough the suspension fluid while blocking passage of the embolization particles.

In some such embodiments, the through-holes are patterned as a plurality of circumferential slits. As used herein, the terms "circumferential slits" and "radial slits" refer to slits having a longitudinal axis perpendicular to the longitudinal axis of the microcatheter. According to some embodiments, the slits are sized and shaped for allowing bending and/or curving of at least part of the microcatheter head with respect to a proximally connected microcatheter body. According to some embodiments, the slits are sized and shaped for allowing bending at a predetermined minimal bending radius while avoiding deformation and/or kinking of the microcatheter head as well as undesired reshaping and/or enlargement of the through-holes which would cause passage of the embolization particles. A non-limiting example of a suitable bending radius may be at about 0.5 mm or at about 1 mm.

In some embodiments, the microcatheters of the present invention are designed and configured for controlled, accurate and/or selective therapeutic embolization and/or angiography of peripheral vessels. Optionally, microcatheters of the present invention are designed and configured to resist, diminish and/or prevent backflow of embolization particles, by generating a fluid barrier proximally to the suspension delivery opening.

In some embodiments, the microcatheters of the present invention are intended for use in angiographic procedures, optionally particularly embolization procedures, and may optionally be applicable for infusing contrast media, therapeutic agents or/and embolic materials to selected sites in the peripheral vascular system. In some embodiments, the microcatheters of the present invention can be used, for example by interventional radiologists, in an interventional radiology suite. In some embodiments, the microcatheters of the present invention are sterile, single-use catheters. In some embodiments, the microcatheters of the present invention may optionally be suitable for limited exposure (<24 hrs) to blood contact. The microcatheters of the present invention may have a hydrophilic coating, for facilitating non-stick vascular navigation, and/or for increased visibility during imaging.

The intended use of embolization microcatheters of the present invention may include one or more of the following steps. The embolization microcatheter is usually brought to its target site using a guiding catheter and/or guidewire in a minimally invasive procedure. Contrast fluid is injected through the guiding catheter and/or the microcatheter, for enhancing fluoroscopic imaging of the artery and its branches, locating the treatment site. Once the target site (e.g. a bleeding or an abnormality) is located, embolization particles are injected into the blood stream via the microcatheter. The particles are carried by the blood flow, thereby creating occlusion of the targeted vessels. Additional contrast fluid may then be injected and x-ray images taken in order to evaluate the success of the procedure i.e. reduced blood flow in the target vessel and/or malformation.

Figure 1:
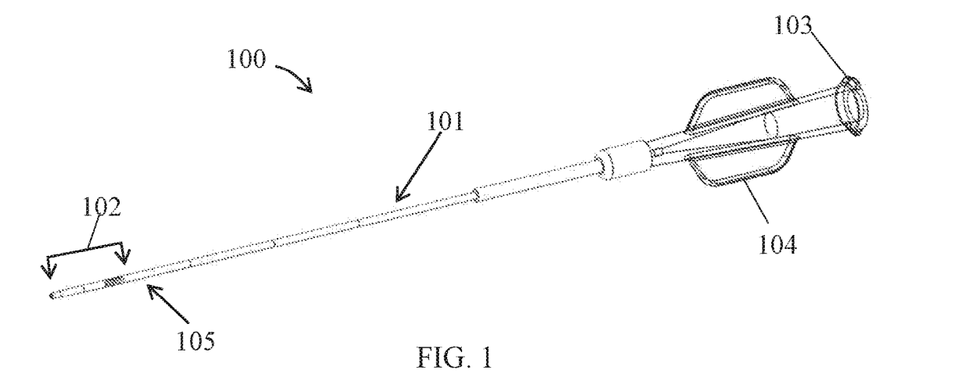
FIG. 1 illustrates an exemplary embolization microcatheter, according to some embodiments of the invention.

FIG. 1 illustrates an exemplary embolization microcatheter 100, which comprises an elongated body 101 and a microcatheter head 102. Elongated microcatheter body 101 is connectable at a proximal end 103 thereof to a suspension reservoir (optionally via a luer taper type fitting 104) and is configured for passing therethrough a premade suspension containing embolization particles suspended in a suspension fluid, from the suspension reservoir.

The length L of microcatheter head 102 is optionally between about 5 and about 30 mm, preferably between about 10 and about 15 mm, with a maximal outer diameter of about 10 mm or less. Microcatheter head 102 is connected to a distal body end 105 of microcatheter body 101 and includes a proximal head section 106, and a distal head section 107 terminating in a head tip 108 (shown for example in FIG. 2A-FIG. 2B). Proximal head section 106 includes a wall 113 forming proximal section lumen 109. Wall 113 includes a plurality of through-holes 110$i$. Distal head section 107 includes a wall 114 forming a distal section lumen 111 sealed to lateral outflow and including a suspension delivery opening 112 located at head tip 108 facilitating frontal outflow.

Each of the side through-holes 110$i$ is shaped and/or sized to allow passage therethrough of suspension fluid while blocking passage of the embolization particles. The embolization microcatheters of the invention may have through-holes having a size and/or shape suitable for a particular intended use e.g. corresponding to the specific beads prescribed for the use. Accordingly, and in order to allow proper utilization for different beads sizes, for example between 20 microns (um) and 900 microns, each through-hole 110$i$ has a smallest cross sectional dimension in a range of between about 15 microns and about 700 microns. In some such embodiments, each of through-holes 110$i$ has a smallest cross sectional dimension in a range of between about 15 microns and about 40 microns (for example, for corresponding with about 50 microns sized beads, or greater), or in a range of between about 40 microns and about 100 microns (for example, for corresponding with about 150 microns sized beads, or greater), or in a range of between about 100 microns and about 700 microns (for example, for corresponding with about 800 microns sized beads, or greater), as essentially described hereinabove. In some embodiments, at least one through-hole 110$i$ has a smallest cross sectional dimension equal to or less than about 50 microns. In some embodiments, at least one through-hole 110$i$ has a smallest cross sectional dimension equal to or more than about 25 microns.

The size and shape of through-holes 110$i$ and of suspension delivery opening 112 is further set to ensure a desired flow distribution between outflow of suspension fluid only via through-holes 110$i$, and the outflow of suspension (fluid and particles) via suspension delivery opening 112. In some embodiments, the total opened area, dimensions and/or shapes of through-holes 110$i$ is chosen so as to maintain a fixed ratio of suspension fluid flow rate, via through-holes 110$i$, relative to suspension fluid flow rate, via suspension delivery opening 112 (optionally while parameters such as overall flow rate, fluid viscosity, remain unchanged). Optionally, alternatively or additionally, dimensions (including length and internal diameter) and/or shape of said proximal section lumen, is so chosen as to maintain a fixed ratio of suspension fluid flow rate, via said through-holes, relative to suspension fluid flow rate, via said suspension delivery opening. Optionally, additionally or alternatively, dimensions (including length and internal diameter)/and/or shape of said distal section lumen, is so chosen as to maintain a fixed ratio of suspension fluid flow rates, via said through-holes, relative to suspension fluid flow rate, via said suspension delivery opening. Optionally, additionally or alternatively, the total open area, dimensions and/or shape of the suspension delivery opening, is so chosen as to maintain a fixed ratio of suspension fluid flow rate, via said through-holes, relative to suspension fluid flow rate, via said suspension delivery opening.

In some embodiments, a total open area of all through-holes 110$i$ is between about 2.5 mm$^2$ and about 7.5 mm$^2$, optionally between about 3 mm$^2$ and about 5 mm$^2$, optionally about 3.5 mm$^2$. In some embodiments, a total open area of suspension delivery opening 112 is between about 0.1 mm$^2$ and about 1 mm$^2$, optionally between about 0.15 mm$^2$ and about 0.3 mm$^2$, optionally about 0.16 mm$^2$. A fixed ratio of suspension fluid flow rates may be in the range of 4:1-1:4, 3:1-1:3; 2:1-1:2 or about 1:1. Each possibility is a separate embodiment.

In some embodiments, a diameter 113 (e.g., minimal diameter) of proximal section lumen 109 is substantially greater than a maximal diameter 'Dmax' of distal section lumen 111. Distal section lumen 111 may include a constricted portion having a constricted diameter 114 equal to or smaller than diameter Dmax, along a constricted length 115 thereof (which may extend at least part of or optionally the entire length of distal section lumen 111 between proximal head section 109 and head tip 108). Constricted length 115 may be about 1 mm or more, optionally about 3 mm or more, optionally about 7 mm or more, optionally about 10 mm or more, optionally about 15 mm or more, optionally about 30 mm or more. Constricted diameter 114 may be from about 1 mm to about 20 mm, optionally particularly about 7 mm or less.

Each of through-holes 110*i* may be in the form of a slit having a width which is less than a minimal diameter of the prescribed particles utilized, so as to block the passage of the particles therethrough. Through-holes 110*i* are distributed radially on proximal head section 106 in a form of a slitted pattern 117. Slitted pattern 117 may be about 2.5 mm to about 7.5 mm in length. Slitted pattern 117 optionally includes a plurality of longitudinally spaced circumferential segments 118*i* (as shown for example in FIG. 5A-FIG. 5C), each circumferential segment including a plurality of circumferentially spaced (radial) slits, such as slit 119*i*. In some embodiments, the length of each of the slits is between about 0.5 mm and about 1 mm. Optionally, each two adjacent slits, such as slits 119*i* and 119*j*, in a particular circumferential segment, such as segment 118*i*, may be spaced by about 50 microns to about 250 microns. Optionally, each two adjacent slits such as slits 119*i* and 119*k*, between two adjacent circumferential segments, such as segments 118*i* and 118*j*, may be spaced by about 50 microns to about 250 microns. Optionally, each two adjacent slits, for example slits 119*i* and 119*k*, between two adjacent circumferential segments, for example segments 118*i* and 118*j*, may be radially offset one with respect to the other i.e. positioned at different circumferential and longitudinal locations on the catheter.

According to some embodiments, the proximal and/or distal end sections may include bending points, such as, but not limited to, micro-slits (also referred to herein as hinges), configured to increase the bendability and maneuverability of the microcatheter within non-straight passages, while preventing (plastic) deformation thereof, particularly in case of relatively long microcatheter heads and/or when utilizing relatively stiff materials and/or materials resistant to bending (such as stiff polymers or elastically resistant metal alloys). According to some embodiments, the bending points may be sized and shaped to prevent substantial outflow of suspension fluid therethrough. In some embodiments, some or all of the through-holes (e.g., slits) can be configured for increasing bendability. In some embodiments, slitted pattern 117 allows improved/increased bending or curving between adjacent circumferential segments, such as segments 118*i* and 118*j*. Such bending or curving optionally allows a maximal bend radius (before kinking of microcatheter head 102) of at least about 0.5 mm, between said head tip relative to said distal body end. Optionally, additionally or alternatively, microcatheter head 102 includes at least one part made of soft, pliable and/or super-elastic material for facilitating a desired bending radius.

In some embodiments, microcatheter head 102 is formed as a single part, or it may be formed from a number of parts (of same or different material or/and mechanical properties). Proximal head section 106 is optionally formed separately to distal head section 107 and assembled thereto when forming said microcatheter head.

Figure 2A:
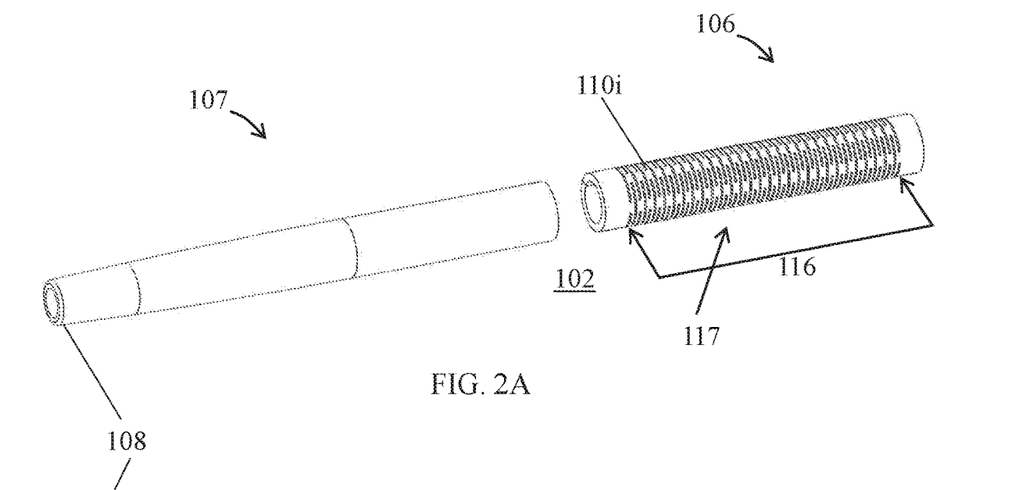
FIG. 2A-FIG. 2B illustrate isometric exploded view and a side cut view, respectively, of a first exemplary microcatheter head, according to some embodiments of the invention.
Figure 2B:
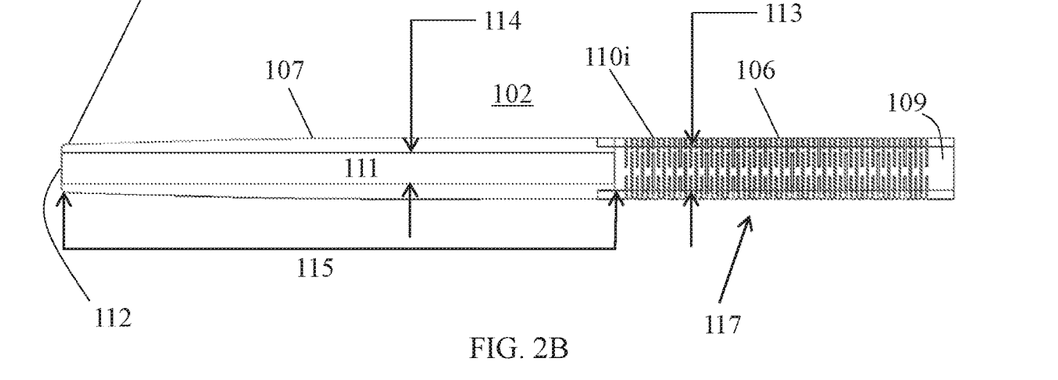

Reference is now made to FIG. 2A and FIG. 2B which illustrate an isometric exploded view and a side cut view, respectively, of an exemplary variation to microcatheter head 102, in which proximal head section 106 is formed of a metal alloy, while distal head section 107 is formed of a polymer. Metal alloys used for forming proximal head section 106 may include: Ni—Ti alloy, stainless steel, cobalt chrome alloy, tungsten alloy, platinum iridium alloy or combinations thereof. Each possibility is a separate embodiment.

Figure 3A:
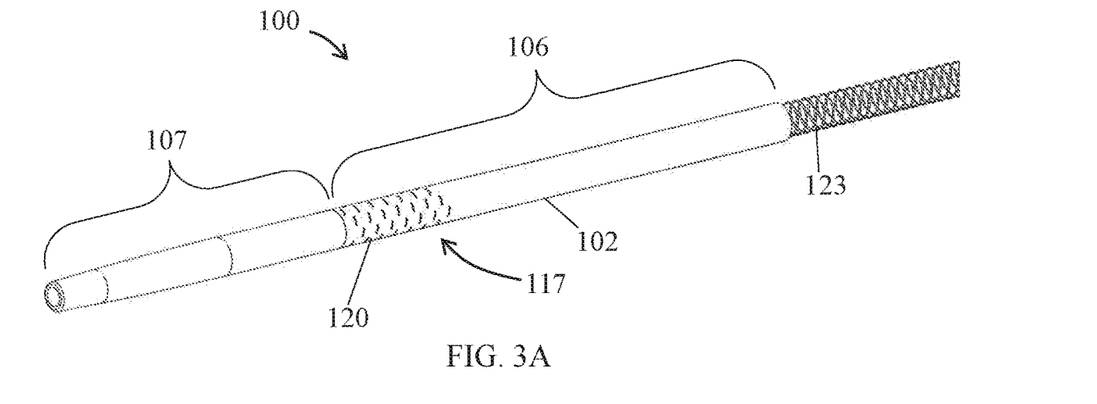
FIG. 3A-FIG. 3B illustrate isometric view and cross sectional view, respectively, of a second exemplary microcatheter head, according to some embodiments of the invention.
Figure 3B:
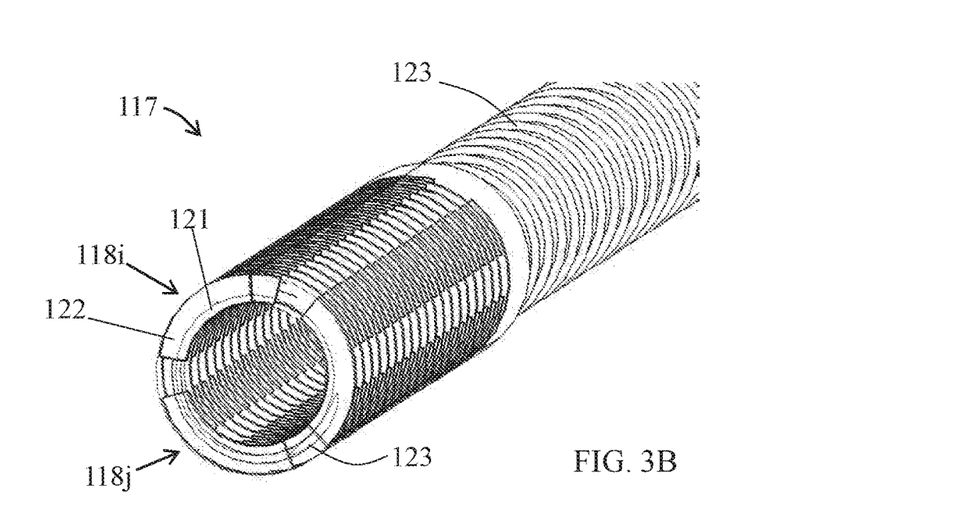

Reference is now made to FIG. 3A- and FIG. 3B, which illustrate an isometric view and a cross sectional view, respectively, of another exemplary variation of microcatheter head 102, in which both proximal head section 106 and distal head section 107 are made from polymer. In some embodiments, proximal head section 106 includes two layers of polymeric tubing 120 concentric and boded with each other to form a wall that is perforated with through-holes 110*i*. Through-holes 110*i* may be formed using laser cutting or chemical photo etching. Polymeric tubing 120 includes an inner polymeric liner 121, optionally made from PTFE, and an outer polymeric extrusion 122, optionally made from thermoplastic elastomer such as thermoplastic polyurethane (such as Pellethane™ TPU by The Lubrizol Corporation, OH, USA) or polyether block amide (such as Pebax™ TPE by Arkema Group, Colombes, France), Nylon, Polyimide, Silicone or any combination thereof. Each possibility is a separate embodiment.

Figure 4A:
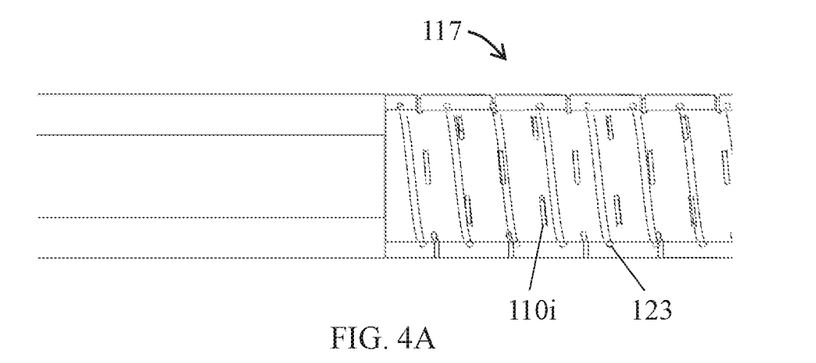
FIG. 4A-FIG. 4C schematically illustrate variations of suitable slitted patterns of through-holes in exemplary microcatheter heads, according to some embodiments of the invention.
Figure 4B:
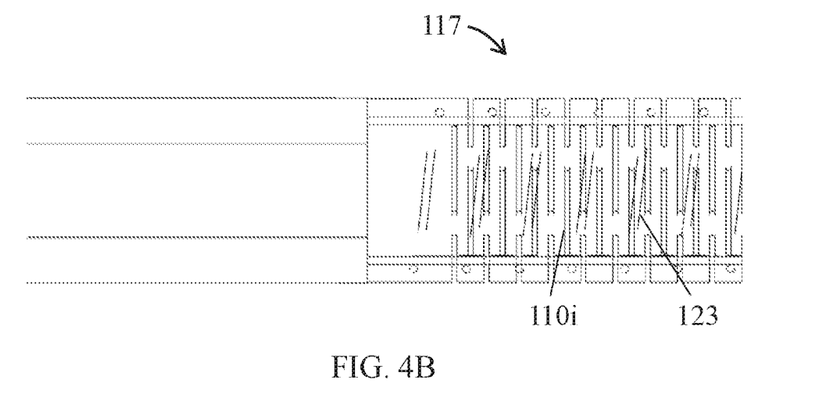
Figure 4C:
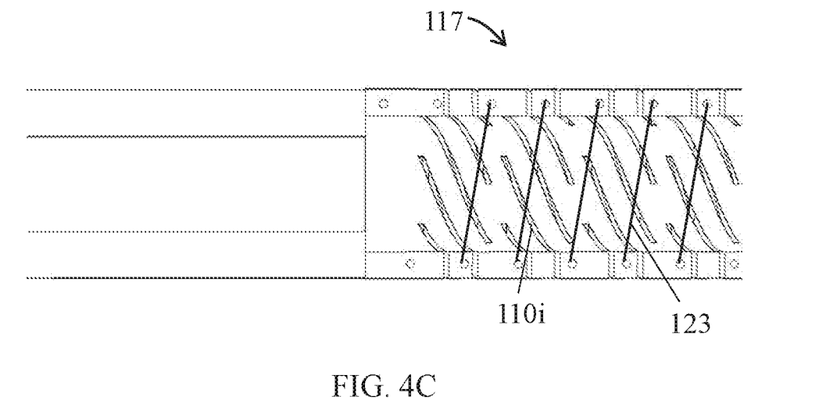
Figures 5A, 5B:
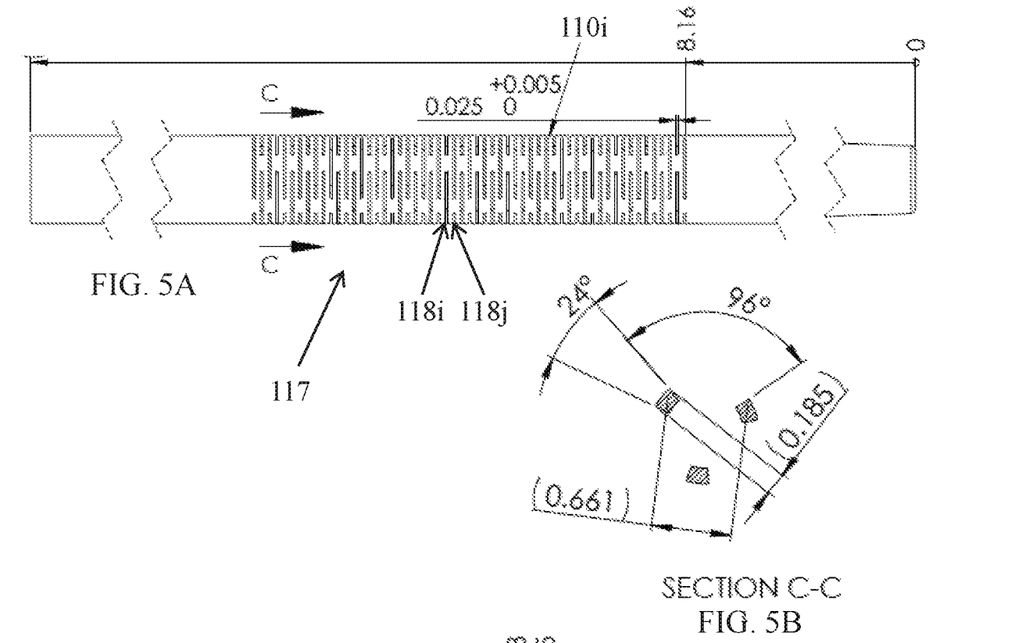
FIG. 5A-FIG. 5C illustrate top view, cross sectional view and a flat pattern (spread) view of an exemplary slitted pattern with exemplary total opened area, dimensions or/and shapes of through-holes, according to some embodiments of the invention.
Figure 5C:
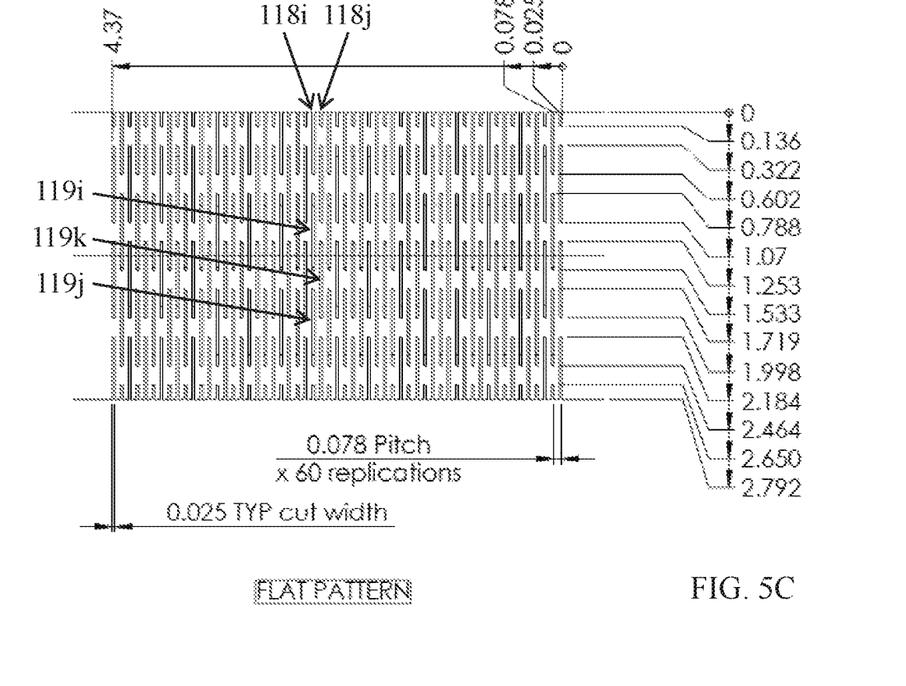

In order to increase resistance to kinking and/or twisting while minimally impacting the desired bending or curving, polymeric tubing 120 may be reinforced with a metal coil 123, which may be made of Tungsten, Stainless steel, Nitinol, Cobalt chrome, Platinum iridium or any other suitable metals or combination of metals. Each possibility is a separate embodiment. Through-holes 110*i* may be formed so as to overlap with the windings of metal coil 123 (for example, as shown in FIG. 4A while leaving the coil intact, also referred to herein as selective cutting). Additionally or alternatively, through-holes 110*i* may be formed in-between windings of metal coil 123 (for example, as shown in FIG. 4B). FIG. 4C shows another variation of slitted pattern 117 where the slits are helical in an opposite direction to windings of coil 123. Coil 123 is optionally assembled in between two polymeric layers (e.g., PTFE inner layer and Pebax outer layer), all reflowed together, followed by applying a hydrophilic coating and then forming slits using laser cutting. Coil 123 can be made of coiled wire/strip or from laser cut tube to the form of coil. FIG. 5A-FIG. 5C illustrate a top view, a cross sectional view and a flat pattern (spread) view of an exemplary variant to slitted pattern 117 for a 2.7 French (equals to about 0.9 mm) sized microcatheter 100 with an outer diameter of about 1 mm, which is configured particularly for embolization particles (beads) sized 40 microns or more. Described in the figures, designs and dimensions of the slits 110*i*. This particular exemplary embodiment of microcatheter 100 and slitted pattern 117 may include at least one of the followings:

> Exemplary constricted length 115—7 mm;
> Exemplary slits length 116—4.37 mm;
> Exemplary constricted diameter 114—0.45 mm;
> Exemplary diameter 113 of proximal section lumen 109—0.64 mm;
> Exemplary width (gap) of each slit 110*i*—25 microns to 32 microns;
> Exemplary arc length of each slit—0.745 mm;
> Exemplary pitch between slits 110*i* in the axial direction—0.078 mm.

Figure 6A:
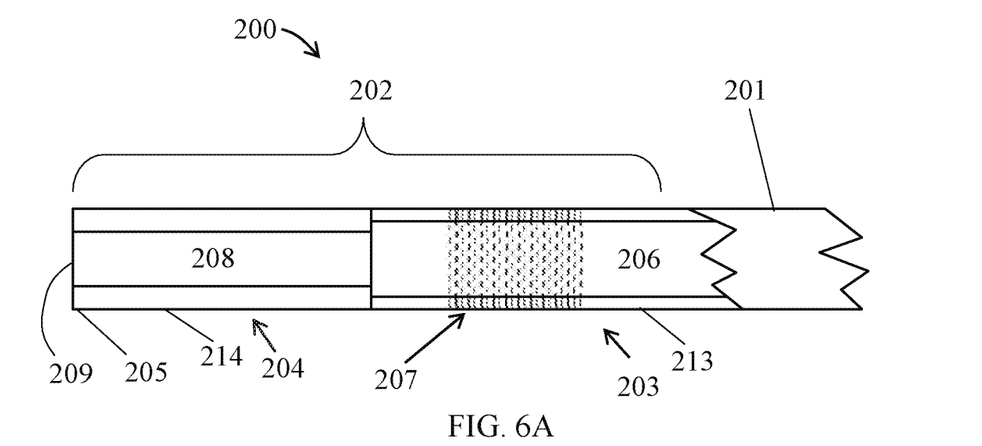
FIG. 6A-FIG. 6B schematically illustrate cross sectional views of an exemplary microcatheter head with an expandable perforated proximal head section, according to some embodiments of the invention.
Figure 6B:
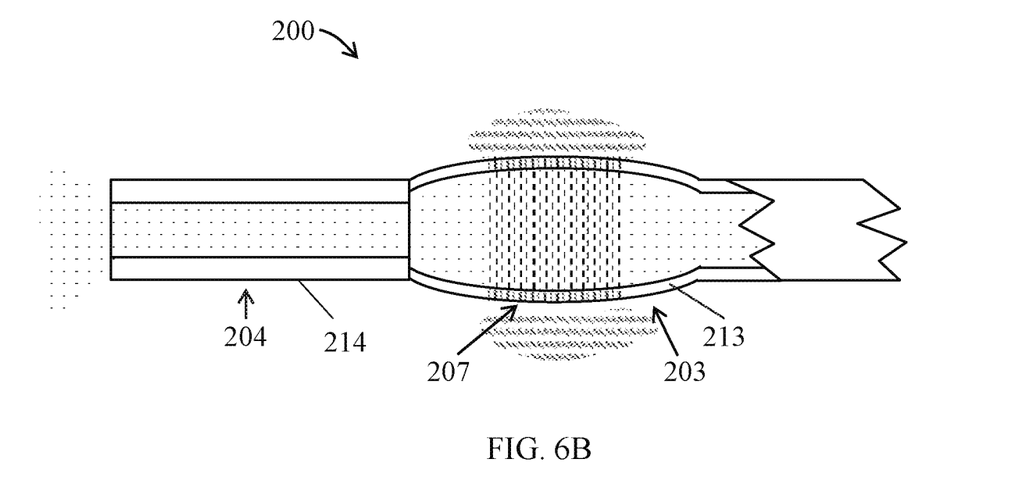

Reference is now made to FIG. 6A and FIG. 6B, which schematically illustrate cross sectional views of an exemplary microcatheter 200 with an expandable perforated proximal head section. Microcatheter 200 includes an elongated microcatheter body 201, configured for passing therein embolization particles suspended in a suspension fluid, and a microcatheter head 202 having a proximal head section 203 and a distal head section 204 ending with a head tip 205.

Proximal head section 203 includes a wall 213 forming proximal section lumen 206. Wall 213 includes through-holes 207, shaped and/or sized to allow passage therethrough of the suspension fluid while blocking passage of the embolization particles. Distal head section 204 includes a wall 214 forming distal section lumen 208 sealed to lateral outflow but terminating with a suspension delivery opening 209 at head tip 205.

Optionally, at least one of through-holes 207 has a smallest cross sectional dimension equal to or less than about 200 microns, or less than about 100 microns, or less than about 50 microns.

Optionally, each through-hole 207 has a form of a slit having a width less than a minimal diameter of the particles, so as to ensure that passage of particles therethrough is blocked.

Optionally side through-holes 207 are distributed along and around a length of proximal head section 203 in a predetermined slitted pattern that includes a plurality of longitudinally spaced circumferential segments, each circumferential segment including a number of circumferentially spaced slits. Optionally, the length of each slit is between about 0.5 mm and about 1 mm.

In some embodiments, wall 213 of proximal head section 203 may be formed from a substantially elastic, expandable material whereas wall 214 of distal head section 204 may be made of a substantially more rigid material. This configuration ensures that proximal head section 203 be configured to expand its inner diameter when suspension fluid is passed therethrough, whereas distal head section 204 substantially maintains its inner diameter.

The expanded inner diameter may optionally be predetermined and set to be substantially larger than maximal inner diameter of distal head section 204, such that the flow rate of the suspension fluid through holes 207 gradually increases along with the expansion of the inner diameter of proximal head section 203, until reaching a desired flow rate ratio between through holes 207 and suspension delivery opening 209, as essentially described herein.

Each of the following terms written in singular grammatical form: 'a', 'an', and 'the', as used herein, means 'at least one', or 'one or more'. Use of the phrase 'one or more' herein does not alter this intended meaning of 'a', 'an', or 'the'. Accordingly, the terms 'a', 'an', and 'the', as used herein, may also refer to, and encompass, a plurality of the stated entity or object, unless otherwise specifically defined or stated herein, or, unless the context clearly dictates otherwise. For example, the phrases: 'a unit', 'a device', 'an assembly', 'a mechanism', 'a component', 'an element', and 'a step or procedure', as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: 'includes', 'including', 'has', 'having', 'comprises', and 'comprising', and, their linguistic/grammatical variants, derivatives, or/and conjugates, as used herein, means 'including, but not limited to', and is to be taken as specifying the stated component(s), feature(s), characteristic(s), parameter(s), integer(s), or step(s), and does not preclude addition of one or more additional component(s), feature(s), characteristic(s), parameter(s), integer(s), step(s), or groups thereof. Each of these terms is considered equivalent in meaning to the phrase 'consisting essentially of'.

The term 'method', as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Throughout this disclosure, a numerical value of a parameter, feature, characteristic, object, or dimension, may be stated or described in terms of a numerical range format. Such a numerical range format, as used herein, illustrates implementation of some exemplary embodiments of the invention, and does not inflexibly limit the scope of the exemplary embodiments of the invention. Accordingly, a stated or described numerical range also refers to, and encompasses, all possible sub-ranges and individual numerical values (where a numerical value may be expressed as a whole, integral, or fractional number) within that stated or described numerical range. For example, a stated or described numerical range 'from 1 to 6' also refers to, and encompasses, all possible sub-ranges, such as 'from 1 to 3', 'from 1 to 4', 'from 1 to 5', 'from 2 to 4', 'from 2 to 6', 'from 3 to 6', etc., and individual numerical values, such as '1', '1.3', '2', '2.8', '3', '3.5', '4', '4.6', '5', '5.2', and '6', within the stated or described numerical range of 'from 1 to 6'. This applies regardless of the numerical breadth, extent, or size, of the stated or described numerical range.

Moreover, for stating or describing a numerical range, the phrase 'in a range of between about a first numerical value and about a second numerical value', is considered equivalent to, and meaning the same as, the phrase 'in a range of from about a first numerical value to about a second numerical value', and, thus, the two equivalently meaning phrases may be used interchangeably. For example, for stating or describing the numerical range of room temperature, the phrase 'room temperature refers to a temperature in a range of between about 20° C. and about 25° C.', and is considered equivalent to, and meaning the same as, the phrase 'room temperature refers to a temperature in a range of from about 20° C. to about 25° C.'.

The term 'about', as used herein, refers to ±10% of the stated numerical value.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment, may also be illustratively described and presented in the context or format of a plurality of separate embodiments.

Although the invention has been illustratively described and presented by way of specific exemplary embodiments, and examples thereof, it is evident that many alternatives, modifications, or/and variations, thereof, will be apparent to those skilled in the art. Accordingly, it is intended that all such alternatives, modifications, or/and variations, fall within the spirit of, and are encompassed by, the broad scope of the appended claims.

All publications, patents, and or/and patent applications, cited or referred to in this disclosure are herein incorporated in their entirety by reference into the specification, to the same extent as if each individual publication, patent, or/and patent application, was specifically and individually indicated to be incorporated herein by reference. In addition, citation or identification of any reference in this specification shall not be construed or understood as an admission that such reference represents or corresponds to prior art of the present invention. To the extent that section headings are used, they should not be construed as necessarily limiting.

The invention claimed is:

1. An embolization microcatheter, comprising:
   an elongated microcatheter body connectable at a proximal end thereof to a suspension reservoir and configured for passing therein a suspension of particles suspended in a suspension fluid; the elongated microcatheter body comprising a distal end opening and at least one layer of polymeric tubing, wherein the polymeric tubing comprises a plurality of longitudinally spaced apart circumferential segments, each circumferential segment comprising a plurality of circumferentially spaced axial slits,
   wherein adjacent segments of the plurality of longitudinally spaced apart circumferential segments are spaced by about 50 microns to about 250 microns,
   wherein each of the plurality of axial slits has a smallest cross sectional dimension in a range of between about 15 microns and about 100 microns and a length in a range of between about 200 microns and about 400 microns,
   wherein each of the plurality of axial slits are shaped and/or sized to allow passage of the suspension fluid while blocking passage of said particles;
   wherein the polymeric tubing comprises an outer polymeric extrusion made from thermoplastic polyurethane; and
   wherein said thermoplastic polyurethane, said smallest cross sectional dimension of the plurality of axial slits, said length of the plurality of axial slits and said spacing of said circumferential segments enable a bending radius of at least 0.5 mm while avoiding kinking of said microcatheter and deformation of the plurality of slits.

2. The embolization microcatheter of claim 1, wherein each said plurality of axial slits has a smallest cross sectional dimension in a range of between about 15 microns and about 50 microns.

3. The embolization microcatheter of claim 1, wherein a maximal outer diameter of the elongated microcatheter body is about 5 mm or less.

4. The embolization microcatheter of claim 1, wherein a total opened area of all the plurality of axial slits is between about 0.1 mm$^2$ and about 7.5 mm$^2$.

5. The embolization microcatheter of claim 1, wherein a total open area of said plurality of axial slits, a dimension/shape of said plurality of axial slits, a dimension/shape of said proximal section lumen, a dimension/shape of said distal section lumen, a total open area of said suspension delivery opening, a dimension/shape of said suspension delivery opening, is so chosen as to maintain a fixed ratio of suspension fluid flow rate, via said axial slits, relative to suspension fluid flow rate, via said suspension delivery opening.

6. The embolization microcatheter of claim 5, wherein said fixed ratio of suspension fluid flow rate via said axial slits, relative to suspension fluid flow rate via said suspension delivery opening in the range of 3:1-1:3.

7. The embolization microcatheter of claim 1, wherein said polymeric tubing includes an inner polymeric liner made from PTFE.

8. The embolization microcatheter of claim 1, wherein each of the plurality of axial slits extend through both the outer polymeric extrusion and the inner polymeric liner.

9. The embolization microcatheter of claim 1, wherein said polymeric tubing is reinforced with a coil.

10. The embolization microcatheter of claim 9, wherein the plurality of axial slits are formed in-between windings of the coil.

11. The embolization microcatheter of claim 9, wherein the plurality of axial slits overlap windings of the coil.

12. The embolization microcatheter of claim 9, wherein the coil is made of tungsten, stainless steel, nitinol, cobalt chrome, or platinum iridium.

13. The embolization microcatheter of claim 9, wherein the coil is embedded within the polymeric tubing.

* * * * *